United States Patent [19]

Ferris et al.

[11] Patent Number: 4,771,128
[45] Date of Patent: Sep. 13, 1988

[54] METHOD OF PURIFYING TOXIN CONJUGATES USING HYDROPHOBIC INTERACTION CHROMATOGRAPHY

[75] Inventors: Robert Ferris, Walnut Creek; Walter J. Laird, Pinole, both of Calif.

[73] Assignee: Cetus Corporation, Emeryville, Calif.

[21] Appl. No.: 917,469

[22] Filed: Oct. 10, 1986

[51] Int. Cl.$^4$ .............................................. C07K 3/18
[52] U.S. Cl. .................... 530/417; 530/412; 530/413; 530/391; 530/388; 530/351; 530/387; 530/370; 424/85; 435/68
[58] Field of Search ............... 530/412, 387, 417, 391, 530/413, 388; 424/85

[56] References Cited

U.S. PATENT DOCUMENTS

| | | | |
|---|---|---|---|
| 3,637,489 | 1/1972 | Haller | 210/31 C |
| 4,259,319 | 3/1981 | Umezawa et al. | 424/117 |
| 4,276,206 | 6/1981 | Katz | 260/6 |
| 4,340,535 | 7/1982 | Voisin et al. | 260/112 B |
| 4,355,023 | 10/1982 | Ehrlich et al. | 424/85 |
| 4,401,592 | 8/1983 | Yoshikumi et al. | 260/112 B |
| 4,461,833 | 7/1984 | Gordon | 435/183 |
| 4,568,488 | 2/1986 | Lee-Huang | 260/112 R |
| 4,579,941 | 4/1986 | Furutani et al. | 536/27 |
| 4,677,197 | 6/1987 | Lin et al. | 530/417 |
| 4,689,401 | 8/1987 | Ferris | 530/396 |

OTHER PUBLICATIONS

Genaud et al, *J. Immunol. Methods*, 49, 1982, pp. 323–332.
Lambert et al, CA, vol. 103, 1985, #1716129.
Robertsons et al, CA, vol. 95, 1981, #127049q.
Zaidenzaig et al, CA, vol. 94, 1981, #11408f.
Pharmacia, pp. 1–12, 1976.
Roennberg et al, CA, vol. 99, 1983, #189394q.
Kunkel et al, *Inf. and Imm.*, 25, 1979, pp. 586–596.
Winter et al, CA, vol. 102, 1985, #107554k.
Regnier, *Science*, 222 (4621): 245–252 (1983).

*Primary Examiner*—John Kight
*Assistant Examiner*—Garnette D. Draper
*Attorney, Agent, or Firm*—Dianne Reed; Gregory Giotta; Albert P. Halluin

[57] ABSTRACT

A method of isolating and purifying toxin conjugates using hydrophobic interaction chromatography. Crude conjugate mixtures are sized to remove unconjugated toxin, and loaded onto a column filled with a suitable hydrophobic gel. Elution is effected with salt solutions of decreasing ionic strength, which salt solutions optionally include increasing amounts of an organic solvent. Toxin conjugate substantially free of unconjugated Ig and unconjugated toxin is provided.

17 Claims, No Drawings

METHOD OF PURIFYING TOXIN CONJUGATES USING HYDROPHOBIC INTERACTION CHROMATOGRAPHY

FIELD OF THE INVENTION

This invention relates generally to chromatographic purification of toxin conjugates, and more particularly relates to a novel method of isolating and purifying immunoconjugates having hydrophobic interaction chromatography.

DESCRIPTION OF THE PRIOR ART

Conjugation of antibodies to toxic drugs and proteins in order to selectively kill tumor cells is an area of research that has recently become of some interest. To a large extent, this is due to the relatively recently developed ability to produce monoclonal antibodies using hybridoma technology, which antibodies are highly specific and can recognize tumor-associated antigens. "Immunoconjugates" may be prepared by covalently linking these antibodies to any of a number of cytotoxic agents. By conjugation, the affinity of the toxins for particular types of tumor cells is increased and the toxins can then exert their effects selectively, by virtue of the specific antibody carriers, against those cells.

Attention has specifically be focused on the highly toxic ribosome-inactivating proteins such as ricin (*Ricin communis,* extracted from castor beans). Preparation of immunoconjugates using these proteins is described, inter alia, in Miyazaki, H., *Gann* 71: 766–774 (1980) and Lambert, J., *J. Bio. Chem.* 260 (22): 12035–12041 (1985)). Ricin consists of two sub-units, termed "A-" and "B-" chains, which are linked by a single disulfide bond. While the A-chain has been shown to be solely responsible for cell death by catalytic inactivation of ribosomes, the B-chain has been demonstrated to provide a binding function, i.e., that chain is able to bind to cell-surface carbohydrates and thus promote the uptake of the A-chain into cells. In order to prepare a suitable immunoconjugate from ricin, then, it is necessary to bind the ricin A-chain to a specific cell-surface binding carrier such as an immunoglobulin (Ig).

Such Ib/ricin A-chain immunoconjugates are known (see, e.g., Miyazaki, supra). Isolation and purification of these immunoconjugates has, however, proved difficult. In prior art methods, while some amount of unreacted A-chain has been removed from the conjugation mixture, unreacted Ig remains in solution, contaminating the immunoconjugate preparation. Other investigators have succeeded in preparing a purified Ig/ricin immunoconjugate; however, that purification process necessitates a multi-step procedure including an ion exchange step (see Lambert, supra). The latter system further requires modification of pH and ionic strength for each conjugate. The present invention is directed to a more versatile and straightforward method of purifying immunoconjugates, which method removes substantially all unreacted antibody and protein from the conjugation mixture. The method uses hydrophobic interaction chromatography as the isolation and purification technique.

Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, e.g., high ionic strength. As the sample is eluted, a descending salt gradient is applied.

SUMMARY OF THE INVENTION

Accordingly, it is an object of the present invention to provide a method of isolating and purifying toxin conjugates using hydrophobic interaction chromatography.

It is another object of the present invention to provide a straightforward and versatile method of removing unreacted Ig from a crude conjugate mixture.

It is still another object of the invention to provide a method of isolating and purifying immunoconjugates purified by hydrophobic interaction chromatography, which immunoconjugates are substantially free of unreacted Ig and have high specific activities.

Additional objects, advantages and novel features of the invention will be set forth in part in the description which follows, andin part will become apparent to those skilled in the art on examination of the following, or may be learned by practice of the invention.

In one aspect of the present invention, immunoconjugates are prepared using known techniques. In preparing these immunoconjugates, monoclonal antibodies of the IgG class produced by hybridoma cells are linked by a disulfide bridge to a ribosome-inactivating or otherwise cytotoxic protein. The conjugate mixture, which contains unconjugated Ig and protein, including cytotoxic protein, as well as the immunoconjugate, is then purified by at least one chromatographic step. This process involves first removing unconjugated protein via sizing chromatography, followed by hydrophobic gel chromatography. In this latter step, the conjugate mixture is loaded onto a column packed with a gel containing hydrophobic groups, which column is capable of selectively retaining materials of different hydrophobic strengths. The individual components of the conjugate mixture are removed by eluting with salt solutions of decreasing ionic strength and, optionally, increasing amounts of a suitable organic solvent. Immunoconjugate substantially free of both unreacted Ig and unreacted cytotoxic protein is provided.

DETAILED DESCRIPTION OF THE INVENTION

The present invention is directed to a novel method of preparing toxin conjugates substantially free of unconjugated protein. This method, in contrast to known methods, is particularly useful in removing unconjugated Ig and unconjugated protein from crude immunoconjugate mixtures.

Immunoconjugates which may be purified by the novel method include ribosome-inactivating proteins such as ricin A linked by a disulfide bridge to an Ig. Other protein toxins may also be linked by similar disulfide bridges, or thioether linkages in some instances, to form the immunoconjugate. Such other toxins include bacterial toxins, e.g., Pseudomonas exotoxin A and Diphtheria toxin, and plant toxins, for example momordin and saponarin. In addition, certain cytokines such as tumor necrosis factor (TNF) are cytotoxic. It has been found, however, that immunoconjugates of PAP, a toxin obtained form *Phytolacca americana,* cannot be purified by the method of the present invention.

Immunoconjugates, for purposes of the invention, may be defined as an antibody or antibody fragments such as Fab and $F(ab')_2$ that selectively bind to an epitope, covalently bound to a protein toxin. More generally, toxin conjugates may be prepared by the method of the invention. A "toxin conjugate", as used herein, means a protein toxin covalently bound to a selective binding molecule. Such selective binding molecules may include, in addition to antibodies and the selective binding fragments thereof mentioned above, hormones, cytokines such as TNF, lymphokines such as interleukin 1 or 2, and cell growth factors such as transferrin, epidermal growth factor and bombesin. Such selective binding molecules bind to receptors found on the target cells to which these molecules bind. Immunoconjugates also selectively bind to cells; however, such binding is based generally upon affinity and avidity for a particular epitope associated with the target cell to which the immunoglobulin portion of the immunoconjugate binds.

While suitable method of preparing such immunoconjugates are known in the art (see, e.g., Miyazaki et al., supra, Lambert et al., supra, and U.S. Pat. No. 4,340,535 to Voisin et al.), a brief summary of the procedure used by applicants follows.

Monoclonal antibodies (designated in the Examples below as MAB260F9) of the IgG class were provided in a phosphate EDTA ($P_iEDTA$) solution containing about 0.10M $Na_2PO_4$ and 1 mM (minimum) EDTA. In order to prepare the antibodies for coupling to the free thiol on the ricin A chain, the Ig was derivatized with DTNB (dithionitrobenzoic acid) and iminothiolane (IT), at about 0° C. for a reaction time of about 24 hours. The Ig-TNB-IT complex was then desalted using a Trisacryl GF-05 column (LKB, Bromma, Sweden) buffered to a pH of about 8.0 with $P_iEDTA$.

Soluble recombinant ricin A (srRTA) was provided by the method described in co-pending application Ser. No. 837,583 for "Recombinant Ricin Toxin Fragments." filed Mar. 7, 1986 and of common assignment herewith. The disclosure of that application is hereby incorporated by reference in its entirety.

The srRTA, at an initial concentration of about 10 mg/ml in $P_iEDTA$ containing 0.1% β-mercaptoethanol (BME), was clarified by centrifugation (~1000 rpm) and desalted on a Trisacryl GF-05 column as above. A free thiol assay was run using DTNB and uv spectroscopy to assay released TND (peak at 412 nm).

The immunoconjugates were then prepared by adding about 10-30 vol. % of glycerol to the srRTA, followed by addition of the Ig-TNB-IT complex. The crude conjugate mixture was allowed to sit at room temperature for about 2 hours, at which time the conjugation process was presumed to be complete.

Purification of the crude conjugate mixture and removal of unconjugated Ig is carried out as follows:

According to the purification method of the present invention, the crude conjugate mixture as prepared above is first loaded onto a sizing column to remove unreacted srRTA and any high molecular weight aggregates. A suitable column for this step is Sephacryl S-300 (Pharmacia, Inc., Piscataway, N.J.), preferably equilibrated prior to use with a phosphate buffer (pH between about 6 and 7). The eluted conjugate mixture, in $P_iEDTA$, is at this point loaded onto a column pre-equilibrated in the same solution as the conjugate mixture outlined above, further containing 1 M NaCl, and packed with a relatively strongly hydrophobic gel such as Phenyl Sepharose CL-4B ® (manufactured by Pharmacia) or TSK Phenyl-5PW (Toyo Soda Kogyo K.K.).

With a Phenyl-Sepharose column, the buffer used in both the sizing step and the subsequent chromatographic separation step preferably contains sodium chloride. With TSK Phenyl-5PW, ammonium solfate is the preferred alternative. Initial concentration of the salt is preferably about 1 M, the concentration used gradually decreasing with each column volume eluting the conjugate from the hydrophobic gel.

Immunoconjugate and unconjugated Ig are then separated and removed from the column as follows. Between about 4 and 10 column volumes of salt solutions (as above) successively decreasing in salt concentration are used to elute the various species. Optionally, increasing concentrations of an organic solvent such as glycerol, ethanol or propylene glycol may be added to the eluant solution to obtain the conjugate mixture in a more concentrated form. Non-conjugated Ig is eluted first, followed by various "mers" (e.g., first by a "1-mer", an Ig conjugated to one A-chain, followed by a "2-mer", an Ig conjugated to two A-chains, etc., up to a "4-mer").

The immunoconjugate so isolated may then if desired be concentrated, e.g. by ultrafiltration, and desalted on a suitable column such as Trisacryl or Sephadex. The desalted immunoconjugate is filtered through a 0.2μ filter. A preferred final concentration of the purified immunoconjugate for medical use is at least about 4 mg/ml, and recoveries on the order of at least about 50-60% are typically obtained with this procedure.

In an alternative embodiment of the invention, a modified hydrophobic gel is provided for a "fast flow" chromatographic separation and purification step. The gel is either Phenyl Sepharose or TSK Phenyl-5PW, preferably Phenyl Sepharose, modified so as to contain only half the number of phenyl groups normally present. Such a modified gel is less hydrophobic, and thus does not bind the conjugate or Ig quite as strongly. Unconjugated Ig is removed with the first column volume of phosphate buffer/salt solution, as described above, and immunoconjugate is removed, typically, with a second column volume of phosphate buffer containing 10-60 vol. % of an organic solvent. In this procedure, the concentration of sodium chloride or ammonium sulfate in the first column volume of eluant, depending on the modified gel selected as above, is about 1.5M. Immunoconjugate is removed in this manner at a concentration of at least about 4 mg/ml, obviating the necessity for a concentration step following removal from the column.

It is to be understood that while the invention has been described in conjunction with the preferred specific embodiments thereof, that the foregoing description as well as the examples which follow are intended to illustrate and not limit the scope of the invention, which is defined by the scope of the appended claims.

EXAMPLE 1

Monoclonal antibodies (designated MAB260F9) of the IgG class were obtained in $P_iEDTA$ (0.10M NaPO$_4$, 1 mM EDTA, pH 8.0) at a concentration of 33.18 mg/ml. Purification was effected using a DEAE Sepharose (Pharmacia) column and ultrafiltration (0.2μ). The Ig was assayed for free thiols using dithionitrobenzoic acid (DTNB) and uv spectrometry to monitor released TNB groups, and it was determined that no free thiol groups were present in the Ig solution. Derivatization with DTNB and iminothiolane (IT) in preparation for coupling to the free thiol or ricin A was then accomplished by adding 363 μl of 1 mM DTNB and 525 μl 10 mM IT to the initial 8.71 ml of Ig. The reaction temperature was maintained at about 0° C. and derivatization was allowed to proceed overnight, i.e. for about 24 hours. The derivatized conjugate was then desalted on a Trisacryl GF-05 column (LKB, Bromma, Sweden) buffered to a pH of 8.0 with $P_iEDTA$ and using a flow rate of about 25 ml/hr.

Soluble recombinant ricin A chain (srRTA) was obtained by the method set forth in co-pending U.S. Patent Application Ser. No. 837,583. The srRTA was provided at an initial concentration of 10 mg/ml in $P_iEDTA$ with 0.1% β-mercaptoethanol (BME) added. Contaminating particulate matter was removed by centrifugation of about 1000 rpm and desalting on a Trisacryl GF-05 column using $P_iEDTA$ and a flow rate of about 25 ml/hr. A free thiol assay was run as described above, and it was determined that approximately 0.73 free thiols were present per molecule of srRTA.

Conjugation was accomplished by adding about 5 ml glycerol to the about 21.1 ml of desalted srRTA, followed by about 10.9 ml of Ig-TNB-IT complex prepared above. The reaction was allowed to proceed at about 25° C. for two hours, at which time it was presumed that conjugation was complete. A free thoil assay at this point gave a 96% conjugation efficiency.

The crude conjugate mixture so obtained was loaded onto a 950-ml Sephacryl S-300 column to remove unreacted srRTA and high molecular weight aggregates. The column was preequilibrated with a sodium chloride/phosphate buffer (pH 6.5; 0.1M $Na_2PO_4$; 1M NaCl; 1 mM EDTA). The conjugate was eluted with the buffer at a flow rate of about 40 ml/hr.

The resulting mixture, containing unconjugated Ig as well as various Ig/srRTA conjugates, was then loaded onto a 70 ml Phenyl Sepharose CL-4B column preequilibrated with the phosphate buffer of the preceding step. The initial conjugate pool was about 262 mg in 126 ml solution. Initial elution of the unreacted Ig was accomplished with a column volume of a 1M NaCl solution at a flow rate of about 20 ml/hr. Various "mers" of the immunoconjugate were then eluted as NaCl solutions of decreasing concentration were applied to the column (gradually decreasing from 1M to 0M), these NaCl solutions also containing increasing amounts of glycerol (gradually increasing from 0 (vol.)% to 60 (vol.)%, beginning with a 1:1 Ig:srRTA conjugate ("1-mer") and ultimately yielding a 1:4 Ig:srRTA conjugate ("4-mer"). The mixture was concentrated by ultrafiltration to about 4 mg/ml, desalted on a Trisacryl column as above, and filtered using a 0.2μ filter. Distribution and purity of the final immunoconjugate preparation was assayed by SDS polyacrylamide gel electrophoresis at: 44.0% 1-mer; 30.8% 2-mer; 10.7% 3-mer; 2.7% 4-mer. Cytoxicity as measured by $TCID_{50}$ (MCF-7 cells): 0.004 nM (minus lactose).

EXAMPLE 2

Immunoconjugate purification using the modified "fast flow" hydrophobic column: MAB260F9 antibodies and srRTA were obtained, purified and conjugated as in Example 1. The conjugate mixture was desalted using a Trisacryl column as described in Example 1, and applied to a hydrophobic gel column as follows.

The hydrophobic gel used in this example was Phenyl Sepharose Cl-4B modified by the manufacturer so as to reduce the standard number of phenyl groups by about 50%. The column (d1 cm; vol.3.14 ml) was equilibrated with 10 column volumes of $P_iEDTA$ solution (0.1M $Na_2PO_4$, 1 mM EDTA) also containing 1.5M NaCl at a pH of about 8.0. The flow rate was set to about 0.13 ml/min and two eluting solutions were prepared: (A) 100 mM $Na_2PO_4$, pH 8.0, 1 mM EDTA, 1.5M NaCl; and (B) 100 mM $Na_2PO_4$, pH 8.0, 60 (vol.) % glycerol. The conjugate mixture was loaded onto the column, and unconjugated Ig was initially removed with solution (A) followed by removal of conjugate with solution (B). The column was then rinsed with 1 column volume of solution (B) to ensure complete removal of immunoconjugate.

EXAMPLE 3

Purification of a TNF Immunoconjugate

Purification of TNF Mutein

*E. coli* cells containing plasmid pAW731 were grown in a suitable growth medium for *E. coli* and were induced to produce TNF. The *E. coli* strain carrying pAW731 has been described in U.S. patent application Ser. No. 753,717, filed July 10, 1985, assigned to the same assignee as the present invention and incorporated herein by reference. The TNF produced by the strain had a single cysteine residue. After induction, the cells were removed from the medium and frozen. The cells were thawed, suspended in 100 ml 0.1M Tris, pH 8, 1 mM EDTA, and sonicated for 30 minutes.

The sonicated cells were centrifuged for 40 min at 12,000 g. The supernatant was removed, adjusted to 0.1M NaCl, and loaded onto a Phenyl Sepharose column previously equilibrated with 0.1M NaCl. The TNF eluted from the column in the flow through, and was dialysed against 0.1M Tris at pH 8.5, 1 mM EDTA. The dialysis retentate was loaded on a DEAE Sepharose column equilibrated with 0.01 M Tris, pH 8.5, 1 mM EDTA, and the TNF was eluted with 0.1M Tris, pH 8.5. The first protein fraction consisted of 95% pure TNF.

Murine monoclonal antibody 317G5 is described in U.S. patent application Ser. No. 690,750, filed Nov. 11, 1985, assigned to the same assignee as the present invention and herein incorporated by reference. 317G5 was derivatized with SPDP as described in U.S. patent application Ser. No. 690,750. Briefly, N-succinimidyl-3-(2-pyridyldithio)propionate (SPDP) was added in a 20-fold molar excess to antibody. Following a 30 minute incubation at room temperature, the unreacted SPDP was removed by dialysis against PBS.

Conjugation

The SPDP-treated antibody was conjugated with TNF. Immediately prior to conjugation, the TNF was reduced with 50 mM dithiothreitol, then desalted on a column of chromatographic resin containing agarose, dextran and/or acrylamide to remove DTT from the protein. Reduced TNF was added in the three to five fold molar excess to the deriatized antibody, and the reaction was allowed to run overnight at 4° C.

The conjugate was loaded onto a Phenyl Sepharose column equilibrated with 2M NaCl and PBS. Free antibody was eluted off the column at 0.5M NaCl. The conjugate and free TNF were eluted off the column with PBS and 30% propylene glycol. Free TNF was separated from the conjugate by size exclusion chromatography using a S-200 Sepharose column.

We claim:

1. A method of purifying immunotoxin conjugates, comprising the steps of:

providing a conjugation mixture containing immunotoxin conjugate, unconjugated selective binding molecule and unconjugated toxin protein;

removing said unconjugated toxin protein from said mixture by gel filtration chromatography;

adding said mixture devoid of said unconjugated toxin protein to a hydrophobic gel chromatograph; and removing said unconjugated binding molecule from said immunotoxin conjugate loaded on a hydrophobic gel with an eluting solution comprising an aqueous salt.

2. The method of claim 1, wherein said step of removing unconjugated toxin on a sizing column precedes said step of removing the unconjugated binding molecule from toxin conjugate.

3. The method of claim 1, wherein said step of removing the unconjugated binding molecule from the immunotoxin conjugate precedes the step of removing unconjugated toxin on a sizing column.

4. The method of claim 2, wherein said toxin protein is a ribosome inactivating protein.

5. The method of claim 4, wherein said toxin protein is ricin toxin A chain.

6. The method of claim 5, wherein said ricin toxin A chain is recombinantly produced.

7. The method of claim 1, wherein said toxin protein is tumor necrosis factor.

8. The method of claim 1, wherein said binding molecule is selected from the group consisting of antibodies and fragments thereof that selectively bind to an epitope, hormones, cytokines, lymphokines and cell growth factors.

9. The method of claim 8, wherein said binding molecule is selected from the group consisting of antibodies and fragments thereof that selectively bind to an epitope.

10. The method of claim 1, wherein said eluting solution comprising an aqueous salt solution contains sodium chloride at a concentration of about 1.0M or less.

11. The method of claim 10, wherein said aqueous salt solution is buffered to a pH ranging from about 6 to about 8.

12. The method of claim 1, wherein said aqueous salt solution is in the range of about four and ten column volumes, each successively decreasing in salt concentration to about 0.5M.

13. The method of claim 1, wherein said salt solution further comprises an organic solvent.

14. The method of claim 12, wherein said column volumes of salt solution include an organic solvent increasing in amount up to about 60 volume percent.

15. The method of claim 14, wherein said organic solvent is selected from the group consisting of glycerol, propylene glycol and ethanol.

16. A method of purifying immunotoxin conjugates, comprising the steps of:

providing a conjugation mixture containing immunoconjugate, unconjugated Ig and unconjugated ricin A chain;

removing said unconjugated ricin A chain from said conjugation mixture by gel filtration chromatography;

loading said mixture devoid of said unconjugated ricin A onto a colum filled with hydrophobic gel; and removing said unconjugated Ig with at least one column volume of an aqueous salt solution.

17. The method of claim 16, wherein said gel is provided with a number of phenyl groups at least sufficient to ensure hydrophobic retention of said conjugate mixture.

* * * * *